US005892082A

United States Patent [19]
Cai et al.

[11] Patent Number: 5,892,082
[45] Date of Patent: Apr. 6, 1999

[54] PROCESS FOR THE PREPARATION OF DIMETHYL TITANOCENE

[75] Inventors: Dongwei Cai, Edison, N.J.; Ian F. Cottrell, Hertfordshire, England; David L. Hughes, Old Bridge; Joseph F. Payack, Somerset, both of N.J.

[73] Assignee: Merck & Co., Inc., Rahway, N.J.

[21] Appl. No.: 813,193

[22] Filed: Mar. 7, 1997

Related U.S. Application Data

[63] Continuation of Ser. No. 708,521, Sep. 5, 1996, abandoned.

[60] Provisional application No. 60/003,352 Sep. 7, 1995.

[30] Foreign Application Priority Data

Feb. 16, 1996 [GB] United Kingdom .................. 9603310

[51] Int. Cl.⁶ .................................................... C07F 13/00
[52] U.S. Cl. .................................................................. 556/53
[58] Field of Search ................................................ 532/53

[56] References Cited

U.S. PATENT DOCUMENTS

| | | |
|---|---|---|
| 2,992,212 | 7/1961 | De Butts . |
| 3,104,249 | 9/1963 | Clauss et al. . |
| 5,087,790 | 2/1992 | Petasis et al. . |
| 5,474,716 | 12/1995 | Lisowsky ............................. 556/53 X |
| 5,523,435 | 6/1996 | Lisowsky ............................. 556/53 X |
| 5,569,746 | 10/1996 | Lee et al. ............................. 556/53 X |
| 5,637,699 | 6/1997 | Dorn et al. . |

FOREIGN PATENT DOCUMENTS 1037446  8/1958  Germany .

OTHER PUBLICATIONS

K. Claus, et al., *Ann. der Chemic:* 654:8 (1962).
A. Glivicky, et al., *Can. J. Chem.,* 51:2609 (1973).
G.A. Razuvaev, et al., *Doklady Akad. Nauk. SSR,* 189: pp. 884–885 (1969).

J. Scholz, et al., *Chem. Ber.,* 120:1369 (1987).

Payack. J. F., et al., *Org. Prep. & Procedures Int'l: New J. of Org. Syn.,* vol. 27, No. 6, pp. 707–709, (Dec. 1995), "An Improved Synthesis of Dimethyltitanocene".

Nifant'ev, I.E., et al., *J. of Organometallic Chem.,* vol. 435, Nos. 1–2, pp. 37–42, (1992), "ansa–Metallocene derivatives of Ti and Zr with the shortest . . . bridge".

Piper, T.S., et al., *J. Inorg. Nucl. Chem.,* vol. 3, pp. 104–124, (1956), Alkyl and Aryl Derivatives of phi–Cyclopentadienyl Compounds of Chromium, Molybdenum . . . .

Chenault, H.K., et al., *J. Org. Chem.,* 59, 6167 (1994).

De Shong, P., et al., *J. Org. Chem.,* 56, 3207 (1991).

Erskine, G.J., et al., *Organomet. Chem.,* 170, 51 (1979).

Kuzmich, D., et al., *J. Am. Chem. Soc.,* 116, 6943 (1994).

Petasis, N.A., et al., *J. Am. Chem. Soc.,* 112, 6392–6394 (1990).

Petasis. N. A., et al., *Tetrahedron Lett.,* 31, 6799 (1990).

Petasis, N. A., et al., *J. Am. Chem. Soc.,* 115, 7208 (1993).

Petasis, N. A., et al., *Tetrahedron Lett.,* 34, 1721 (1993).

Petasis, N. A., et al., *Tetrahedron Lett.,* 36, 2393 (1995).

Swenton, J.S., et al., *J. Org. Chem.,* 56, 6156 (1991).

*Primary Examiner*—Paul F. Shaver
*Attorney, Agent, or Firm*—J. Eric Thies; David L. Rose

[57] ABSTRACT

The present invention is directed to a process for the preparation of the reagent dimethyl titanocene $(Cp_2Ti(CH_3)_2)$ from titanocene dichloride $(Cp_2TiCl_2)$ and a methyl magnesium halide, in particular, methyl magnesium chloride $(CH_3MgCl)$. The instant process provides the desired reagent in a manner which is generally less hazardous and more economical than previous methods.

22 Claims, No Drawings

PROCESS FOR THE PREPARATION OF DIMETHYL TITANOCENE

This application is a continuation of application Ser. No. 08/708,521, filed Sep. 5, 1996, now abandoned, which claims priority under 35 U.S.C. § 119(e) from application Ser. No. 60/003,352, filed Sep. 7, 1995.

BACKGROUND OF THE INVENTION

Dimethyl titanocene is an effective methylenating reagent for a variety of carbonyl compounds, including esters and lactones (N. A. Petasis and E. I. Bzowej, *J. Am. Chem. Soc.*, 112, 6392–6394 (1990)). The reagent has been used to methylenate heteroatom-substituted carbonyls, and is also a ring-opening metathesis polymerization catalyst (N. A. Petasis and S.-P. Lu, *Tetrahedron Lett.*, 36, 2393 (1995); N. A. Petasis and D.-K. Fu, *J. Am. Chem. Soc.*, 115, 7208 (1993)). Accordingly, it is well recognized in the art that dimethyl titanocene has become a valuable synthetic tool. See for example the extensive use of dituethyl titanocene by e.g., N. A. Petasis and M. A. Patane, *Tetrahedron Lett.*, 31, 6799 (1990); P. DeShong and P. J. Rybczynski, *J. Org. Chem.*, 56, 3207 (1991); J. S. Swenton, D. Bradin, B. D. Gates, *J. Org. Chem.*, 56, 6156 (1991); N. A. Petasis and E. I. Bzowej, *Tetrahedron Lett.*, 34, 1721 (1993); H. K. Chenault and L. F. Chafin, *J. Org. Chem.*, 59, 6167 (1994); D. Kuzmich, S. C. Wu, D.-C. Ha, C.-S. Lee, S. Ramesh, S. Atarashi, J.-K. Choi and D. J. Hart, *J Am. Chem. Soc.*, 116, 6943 (1994); U.S. Pat. No. 5,087,790 (1992); and C. Dorn, et al., *PCT Patent Publication* WO 95/16679 (1995).

Although synthetic methodology may require the availablity of this reagent on a multi-kilogram scale, the published preparation procedure for the preparation of dimethyl titanocene is not amenable to large scale operations (K. Claus and H. Bestian, *Justus Liebigs Ann. Chem.*, 654, 8 (1962)). The reference protocol calls for methylating titanocene dichloride with the pyrophoric reagent methyl lithium in ether, followed by an aqueous quench, and then a work-up where the material was isolated as a solid. However, it has been noted that $Cp_2Ti(CH_3)_2$ is unstable in the solid phase, and evaporation of solutions containing the reagent have decomposed unpredictably (for a discussion of the solid state stability of dimethyl titanocene see: G. J. Erskine, J. Hartgerink, E. L. Weinberg and J. D. McCowan *J. Organomet. Chem.*, 170, 51 (1979) and references cited therein). The preparation of dimethyl titanocene from methylmagnesium iodide and dichlorotitanocene in diethyl ether has been reported in German Patent Publication No. 1,037, 446 (1959) to Farbwerke Hoechst, however, few details of the procedure are provided, and a yield of only 58% is reported.

Accordingly, there is a need in the art for a safer and more economical method for the preparation of dimethyl titanocene. The present invention provides a safer method for the preparation of dimethyl titanocene in high yield from titanocene dichloride and methyl magnesium chloride. The present process avoids the use of methyl lithium which is a pyrophoric reagent and hazardous to use on a large scale. Methylmagnesium chloride is safer to use than methyl-lithium and is also less expensive.

SUMMARY OF THE INVENTION

The present invention is directed to a process for the preparation of a reagent which is useful in synthetic organic chemistry. In particular, the present invention is directed to a process for the preparation of the reagent dimethyl titanocene $(Cp_2Ti(CH_3)_2)$ from titanocene dichloride $(Cp_2TiCl_2)$ and a methyl magnesium halide, in particular, methyl magnesium chloride $(CH_3MgCl)$. The instant process provides the desired reagent in a manner which is generally less hazardous and more economical than previous methods known in the art.

DETAILED DESCRIPTION OF THE INVENTION

The present invention is directed to a process for the preparation of the reagent dimethyl titanocene $(Cp_2Ti(CH_3)_2)$ from titanocene dichloride $(Cp_2TiCl_2)$ and a methyl magnesium halide, selected from the group consisting of: methyl magnesium chloride $(CH_3MgCl)$ (MeMgCl); methyl magnesium bromide $(CH_3MgBr)$; and methyl magnesium iodide $(CH_3MgI)$. In a preferred embodiment, the methyl magnesium halide is methyl magnesium chloride $(CH_3MgCl)$.

In one embodiment, this invention is directed to a process for the preparation of dimethyl titanocene which comprises:
reacting titanocene dichloride with methyl magnesium chloride in a reaction mixture which comprises an inert solvent.

In the instant process the inert solvent may be selected from the group consisting of: benzene; toluene; xylene (including o-xylene, m-xylene, p-xylene, and mixtures thereof); petroleum ether; hexane; heptane; cumene; mesitylene; diethyl ether; tetrahydrofuran; digylme (2-methoxyethyl ether); methyl-t-butyl ether; a chlorinated hydrocarbon such as dichloromethane, chloroform, carbon tetrachloride, dichloroethane, chlorobenzene, ortho-dichlorobenzene; and the like; and mixtures thereof. In a preferred embodiment, the inert solvent comprises a solvent selected from toluene, xylene and benzene, and which may additionally comprise tetrahydrofuran. In a more preferred embodiment, the inert solvent comprises a solvent which is toluene, and which may additionally comprise tetrahydrofuran. Other ingredients may be present in the reaction mixture, for example, to facilite the preparation of dimethyl titanocene or to monitor the progress of the reaction.

The instant process may be conducted within a temperature range of between about −20° and about 25° C., wherein the more prefered temperature range is between about −10° and about 15° C. and the most preferred temperature range is between about −5° and about 10° C.

In the instant process the molar ratio of methyl magnesium chloride to titanocene dichloride is typically in the range of from about 2:1 to about 3:1, preferably about 2:1 to about 2.5:1, and more preferably about 2.2:1 to about 2.4:1.

In a prefered embodiment of the instant process, following the reaction of titanocene dichloride with methyl magnesium chloride, the reaction mixture is subsequently contacted with an aqueous solution to quench the reaction. The aqueous solution generally comprises a weakly acidic solution, for example, an aqueous solution of ammonium chloride or an aqueous solution of sodium phosphate buffer. Preferably the reaction mixture is subsequently added to an aqueous solution which comprises ammonium chloride. The ammonium chloride is preferably present in a concentration of about 1–50% (w/v), more preferably in a concentration of about 4–20% (w/v) and even more preferably in a concentration of about 6–10% (w/v).

"Dimethyl titanocene" is represented by the formula $Cp_2Ti(CH_3)_2$, wherein "Cp" indicates the presence of a cyclopentadienyl (cyclopentadienylide) ("$C_5H_5$") group. In particular, dimethyl titanocene has the following chemical structure:

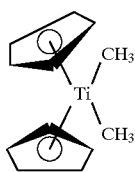

One of the starting materials for the present process di(cyclopentadienyl)titanium dichloride (titanocene dichloride) is represented by the formula $Cp_2TiCl_2$, wherein "Cp" indicates the presence of a cyclopentadienyl (cyclopentadienylide) ("$C_5H_5$") group. The other starting material methyl magnesium chloride is represented by the formula MeMgCl or $CH_3MgCl$. Both of the starting materials titanocene dichloride and methyl magnesium chloride are commercially available.

In a typical prefered procedure, a solution of methyl magnesium chloride ($CH_3MgCl$) in tetrahydrofuran is added to a solution of titanocene dichloride ($Cp_2TiCl_2$) in toluene at an initial temperature of about $-5°$ C. over a period of about 1 hour, while maintaining the temperature below about $8°-10°$ C. The resulting slurry is aged at $0°-5°$ C. for about 1 hour, or until the slightly soluble dimethyl titanocene ($Cp_2TiCl_2$) has dissolved. Upon completion of the reaction, the reaction mixture is poured into approximately 6–10% aqueous ammonium chloride. After several water and brine washes, the dried organic layer is concentrated to about half the original volume, and is assayed by NMR and used as is for subsequent reactions (typical assays indicate 12–17 wt % of reagent in solution). It is noted that solutions of dimethyl titanocene in toluene with 10% added THF have been found to be stable at $0°$ C. for at least several months. The instant process has been repeated several times on a multi-kilogram scale giving yields in appproximately the 85–90% range.

The preparation of the desired compound with the process of the present invention may be carried out in sequential or convergent synthetic routes. It is noted that in some cases the order of carrying out the subject reactions may be varied to facilitate the reaction or to avoid unwanted reaction products. In general, the process of the present invention is conducted in a sequential manner as presented herein.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

NMR spectra were run in $CDCl_3$ and the $^1H$ and $^{13}C$ spectra were measured at 250 and 62.9 MHz. The proton spectra were run with a 10 s delay between pulses for the wt % assay. Toluene was dried to less than 150 μg/mL water (by Karl Fisher titration) with 3 Å sieves. Titanocene dichloride and methyl magnesium chloride were purchased from Boulder Scientific and were used as received. Standard inert atmosphere techniques were used for the reaction and work-up.

EXAMPLE 1

To a well stirred slurry of titanocene dichloride ($Cp_2TiCl_2$) (6.0 g, 24.1 mmol) in toluene (72 mL) chilled to $-5°$ C. was added dropwise methyl magnesium chloride ($CH_3MgCl$) (19.8 g, 19.2 mL, 3.0M in THF, 57.6 mmol, 2.4 eq) over 10 min, maintaining the temperature below $5°$ C. A viscous slurry was formed as magnesium chloride precipitated. The resulting slurry was aged at $0°-5°$ C. for 50 min, during which time the insoluble red $Cp_2TiCl_2$ had dissolved. A NMR assay on a quenched sample was taken to confirm reaction completion. A 0.2 mL sample was quenched into 1 mL of water and 1 ml of $CDCl_3$. The chloroform layer was used directly for NMR analysis. Dimethyl titanocene has resonances at 6.0 ppm (Cp) group and $-0.2$ ppm ($CH_3$ group). The monomethyl compound has resonances 0.2–0.3 ppm downfield, and the titanocene dichloride has resonance at 6.5 ppm.

The reaction was thne quenched by addition of a solution of 10% aqueous ammonium chloride (20 mL) over 10 min, maintaining the temperature below $10°$ C. The layers were separated and the organic phase was washed with cold water (3×20 mL) and brine (20 mL), then was dried with $Na_2SO_4$ (20 g). The filtered organic layer was concentrated under vacuum to approximately half volume. The total weight of the solution was 43 g, and NMR analysis showed 11.2 wt % in dimethyl titanocene (4.8 g, 96% yield). The THF level was 2%, however, the presence of a small amount of THF increases the stability of the compound. The material was stored under nitrogen at $0°$ C.

EXAMPLE 2

To a well stirred slurry of titanocene dichloride ($Cp_2TiCl_2$) (249 g, 1.00 mol) in toluene (2.75 L) chilled to $-5°$ C. (internal temp) was added methyl magnesium chloride ($CH_3MgCl$) (750 mL, 3.0M in THF, 2.25 mol) over 1 h, maintaining the temperature below $8°$ C. The resulting orange slurry is aged at $0°-5°$ C. for 1 h, or until the insoluble purple $Cp_2TiCl_2$ has dissolved. A NMR was taken to confirm reaction completion (see below), then the reaction was quenched into a solution of 6% aqueous ammonium chloride (700 mL), maintained at $0°-5°$ C. The layers were separated and the organic phase was washed with cold water (3×575 mL) and brine (575 mL), then was dried with $Na_2SO_4$ (220 g). The filtered organic layer was evaporated to 1.5 Kg (maintaining an internal temperature of $25°$ or less). Weight % assay by $^1H$ NMR showed the solution to contain 187 g product (90%, 12.5 wt % solution in toluene/THF). Typically, the material was greater than 95% pure, with only traces of the starting material and monomethyl intermediate. The solution may be further concentrated to 1.0 Kg, giving a 18 wt % solution in toluene, allowing for an easier assay. However, the presence of a small amount of THF increases the stability of the compound. The material was stored under nitrogen in a sealed carboy at $0°$ C. $^1H$ NMR $Cp_2Ti(CH_3)_2$: δ 6.05 (s, 10H), $-0.05$ (s, 6H). $Cp_2TiCl(CH_3)$: δ 6.22 (s, 10H), 0.80 (s, 3H). $Cp_2TiCl_2$: δ 6.56 (s, 10H). $^{13}C$ NMR $Cp_2Ti(CH_3)_2$: δ 113.20 ($Cp_2$), 45.77 (($CH_3$)$_2$). $Cp_2TiClCH_3$: δ 115.86 ($Cp_2$), 50.37 ($CH_3$). $Cp_2TiCl_2$: δ 120.18.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of dimethyl titanocene which comprises:

reacting titanocene dichloride with methyl magnesium chloride in a reaction mixture which comprises an inert solvent.

2. The process of claim 1 wherein the reaction mixture comprises an inert solvent selected from the group consisting of:

benzene; toluene; xylene; petroleum ether; hexane; heptane; cumene; mesitylene; diethyl ether; tetrahydrofuran; digylme; methyl-t-butyl ether; dichloromethane; carbon tetrachloride; dichloroethane; chlorobenzene; ortho-dichlorobenzene; and mixtures thereof.

3. The process of claim 2 wherein the inert solvent is selected from the group consisting of:

toluene; xylene; and benzene.

4. The process of claim 3 wherein the inert solvent additionally comprises tetrahydrofuran.

5. The process of claim 2 wherein the inert solvent is toluene.

6. The process of claim 5 wherein the inert solvent additionally comprises tetrahydrofuran.

7. The process of claim 1 wherein the temperature range is between about −20° and about 25° C.

8. The process of claim 7 wherein the temperature range is between about −10° and about 15° C.

9. The process of claim 8 wherein the temperature range is between about −5° and about 10° C.

10. The process of claim 1 wherein the molar ratio of methyl magnesium chloride to titanocene dichloride is in the range of from about 2:1 to about 3:1.

11. The process of claim 10 wherein the molar ratio of methyl magnesium chloride to titanocene dichloride is in the range of from about 2:1 to about 2.5:1.

12. The process of claim 11 wherein the molar ratio of methyl magnesium chloride to titanocene dichloride is in the range of from about 2.2:1 to about 2.4:1.

13. The process of claim 1 wherein the reaction mixture is subsequently contacted with an aqueous solution.

14. The process of claim 13 wherein the aqueous solution comprises ammonium chloride or sodium phosphate buffer.

15. The process of claim 1 wherein the reaction mixture is subsequently contacted with an aqueous solution which comprises ammonium chloride.

16. The process of claim 15 wherein the ammonium chloride is present in a concentration of about 1–50% (w/v).

17. The Process of claim 16 wherein the ammonium chloride is present in a concentration of about 4–20% (w/v).

18. The process of claim 17 wherein the ammonium chloride is present in a concentration of about 6–10% (w/v).

19. The process of claim 1 for the preparation of dimethyltitanocene which comprises:

reacting titanocene dichloride with methyl magnesium chloride at a molar ratio of from about 2.2:1 to about 2.4:1 in a reaction mixture which comprises toluene and tetrahydrofuran at a temperature range of between about −5° and about 10° C.

20. The process of claim 19 wherein the reaction mixture is subsequently contacted with an aqueous solution which comprises ammonium chloride in a concentration of about 6°–10 ° C. (w/v).

21. A process for the preparation of dimethyl titanocene which comprises:

reacting titanocene dichloride with methyl magnesium chloride at a molar ratio of from about 2:1 to about 2.5:1 in a reaction mixture which comprises toluene and tetrahydrofuran at a temperature range of between about −10° and about 15° C.

22. A process for the preparation of dimethyl titanocene which comprises:

reacting titanocene dichloride with methyl magnesium chloride at a molar ratio of from about 2.2:1 to about 2.4:1 in a reaction mixture which comprises toluene and tetrahydrofuran at a temperature range of between about −5° and about 10° C.; and subsequently contacting the reaction mixture into an aqueous solution which comprises ammonium chloride in a concentration of about 4°–20 ° C. (w/v).

* * * * *